(12) United States Patent
Sehsah et al.

(10) Patent No.: US 11,634,878 B2
(45) Date of Patent: Apr. 25, 2023

(54) SYSTEMS FOR OFFSHORE ENVIRONMENTAL MAINTENANCE

(71) Applicant: Saudi Arabian Oil Company, Dhahran (SA)

(72) Inventors: Ossama R. Sehsah, Dhahran (SA); Mahmoud Adnan Alqurashi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 855 days.

(21) Appl. No.: 16/534,914

(22) Filed: Aug. 7, 2019

(65) Prior Publication Data
US 2021/0040702 A1 Feb. 11, 2021

(51) Int. Cl.
| | | |
|---|---|---|
| E02B 15/04 | (2006.01) | |
| G01N 33/28 | (2006.01) | |
| G01N 33/18 | (2006.01) | |
| B63B 35/32 | (2006.01) | |
| B63G 8/00 | (2006.01) | |
| E02B 15/10 | (2006.01) | |
| G01N 33/24 | (2006.01) | |

(52) U.S. Cl.
CPC ............ *E02B 15/045* (2013.01); *B63B 35/32* (2013.01); *B63G 8/001* (2013.01); *E02B 15/10* (2013.01); *G01N 33/1833* (2013.01); *G01N 33/1886* (2013.01); *G01N 33/241* (2013.01); *G01N 33/28* (2013.01); *B63G 2008/004* (2013.01); *B63G 2008/005* (2013.01)

(58) Field of Classification Search
CPC .............. B63B 35/32; B63G 2008/004; B63G 2008/005; B63G 8/001; E02B 15/045; E02B 15/10; G01N 33/18; G01N 33/1833; G01N 33/1886; G01N 33/241; G01N 33/28
USPC .................................. 436/39, 40, 60; 701/21
See application file for complete search history.

(56) References Cited

U.S. PATENT DOCUMENTS

| | | |
|---|---|---|
| 5,075,014 A | 12/1991 | Sullivan |
| 2007/0261629 A1 | 11/2007 | Choi |
| 2008/0135494 A1 | 6/2008 | Usher |

(Continued)

FOREIGN PATENT DOCUMENTS

| | | | |
|---|---|---|---|
| WO | 2014/035749 | * | 3/2014 |
| WO | 2018176106 | | 10/2018 |
| WO | 2018231273 | | 12/2018 |

OTHER PUBLICATIONS

PCT International Search Report and Written Opinion in International Application No. PCT/US2020/045,330, dated Nov. 26, 2020, 14 pages.

(Continued)

*Primary Examiner* — Maureen Wallenhorst
(74) *Attorney, Agent, or Firm* — Fish & Richardson P.C.

(57) ABSTRACT

Systems, methods, and apparatuses for detecting and collecting fluids released into a body of water are disclosed. Particularly, detection and collection of a fluid released during a petroleum exploration or production operation are disclosed. A released fluid may be detected using sensors on a submersible vehicle (SV) or a plurality of SVs operating in concert. A detected released fluid is collected in storage tanks onboard of the one or more SVs or in an external tank coupled to the one or more SVs.

22 Claims, 5 Drawing Sheets

(56) References Cited

U.S. PATENT DOCUMENTS

| | | | | |
|---|---|---|---|---|
| 2012/0267115 | A1* | 10/2012 | Brown | E21B 41/0007 |
| | | | | 166/107 |
| 2013/0105148 | A1* | 5/2013 | Coats | E21B 47/01 |
| | | | | 166/250.01 |
| 2014/0284465 | A1* | 9/2014 | Pottorf | G01V 9/007 |
| | | | | 250/253 |
| 2015/0175452 | A1 | 6/2015 | Nedwed et al. | |
| 2015/0192437 | A1* | 7/2015 | Bouzas | G06F 9/00 |
| | | | | 701/1 |
| 2018/0067228 | A1 | 3/2018 | Nali et al. | |
| 2019/0352694 | A1* | 11/2019 | Pilloni | G01N 1/02 |

OTHER PUBLICATIONS

GCC Examination Report issued in Gulf Cooperation Council Appln. No. 2020-40257, dated Sep. 29, 2021, 3 pages.

Buyrov.com' [online], "Charpie: The best ROV manufacturer," available on or before 2017, retrieved on Jun. 27, 2019, retrieved from URL <www.buyrov.com/>, 5 pages.

Exploration.marinersmuseum.org' [online], "ROV", available on or before May 2019, retrieved on Jun. 27, 2019, retrieved from URL <https://exploration.marinersmuseum.org/object/rov/>, 3 pages.

Phys.org', [online], "Team develops underwater robot to assist in oil-spill cleanup," Phys Org, Mar. 16, 2015, 3 pages.

Rigzone.com', [online], "How Do ROVs Work?" available on or before 1999, retrieved on Jun. 27, 2019, retrieved from URL <https://www.rigzone.com/training/insight.asp?insight_id=343&c_id=>, 5 pages.

* cited by examiner

SYSTEMS FOR OFFSHORE ENVIRONMENTAL MAINTENANCE

TECHNICAL FIELD

This present disclosure relates to environmental remediation in offshore oil production.

BACKGROUND

Gas flaring (referred to hereinafter as "flaring") involves the combustion of unwanted or excess gases, liquids, or both, that are released during normal or unplanned over-pressuring operations in many industrial processes, such as oil-gas extraction. During the course of flaring, unburned quantities of oil can be ejected from an oil producing operation, such as an offshore oil exploration and production operation. The expelled, unburned oil collects in the water, posing a potential environmental hazard and resulting in a loss of revenue.

SUMMARY

A first aspect of the present disclosure is directed to a computer-implemented method performed by one or more processors for detecting and collecting a fluid released into a body of water during a petroleum exploration or production operation. The method may include detecting the presence of a released fluid in a body of water with a submersible vehicle (SV) and collecting a detected released fluid in the body of water with the SV.

Another aspect of the present disclosure is directed to a system for detecting and collecting a fluid released into a body of water during a petroleum exploration or production operation. The system may include a system for detecting and collecting a fluid released into a body of water during a petroleum exploration or production operation and a non-transitory computer-readable storage medium coupled to the one or more processors and storing programming instructions for execution by the one or more processors. The programming instructions instruct the one or more processors to detect the presence of a released fluid in a body of water with a submersible vehicle (SV) and collect a detected released fluid in the body of water with the SV.

Another aspect of the present disclosure is directed to a computer program product encoded on a non-transitory medium. The product may include computer readable instructions for causing one or more processors to perform operations including detecting the presence of a released fluid in a body of water with a submersible vehicle (SV) and collecting a detected released fluid in the body of water with the SV.

The various aspects may include one or more of the following features. The SV may be introduced into the body of water prior to release of the released fluid. Detecting the presence of a released fluid in a body of water with an SV may include sensing rheological properties of the released fluid with one or more sensors of the SV. Collecting a detected released fluid in the body of water with the SV may include activating a fluid collection system of the SV. Collecting a detected released fluid in the body of water with the SV may include collecting the detected released fluid in storage tank onboard of the SV or in an external tank that is external of the SV. Detecting the presence of a released fluid in a body of water may include comparing rheological properties sensed with one or more sensors of the SV to a database of rheological properties associated with known fluids and identifying the released fluid as one of the known fluids whose rheological properties correspond to the sensed rheological properties. Detecting the presence of a released fluid in a body of water with a submersible vehicle (SV) may include detecting the presence of the released fluid in the body of water with a plurality of SVs operating in concert with each other. The presence of the released fluid may be sensed while collecting the detected released fluid in the body of water with the SV.

The various aspects may also include one or more of the following features. Programming instructions may also include programming instructions to instruct the one or more processors to introduce the SV into the body of water prior to release of the released fluid. The programming instructions operable to instruct the one or more processors to detect the presence of a released fluid in a body of water with an SV may include programming instructions operable to instruct the one or more processors to sense rheological properties of the released fluid with one or more sensors of the SV. The programming instructions operable to instruct the one or more processors to collect a detected released fluid in the body of water with the SV may include programming instructions to instruct the one or more processors to activate a fluid collection system of the SV. The programming instructions operable to instruct the one or more processors to collect a detected released fluid in the body of water with the SV may include programming instructions operable to instruct the one or more processors to collect the detected released fluid in storage tank onboard of the SV or in an external tank that is external of the SV. The programming instructions operable to instruct the one or more processors to detect the presence of a released fluid in a body of water may include programming instructions operable to instruct the one or more processors to compare rheological properties sensed with one or more sensors of the SV to a database of rheological properties associated with known fluids and identify the released fluid as one of the known fluids whose rheological properties correspond to the sensed rheological properties. The programming instructions operable to instruct the one or more processors to detect the presence of a released fluid in a body of water with a submersible vehicle (SV) may include programming instructions operable to instruct the one or more processors to detect the presence of the released fluid in the body of water with a plurality of SVs operating in concert with each other. The programming instructions may include programming instructions operable to instruct the one or more processors to sense for the presence of the released fluid while collecting the detected released fluid in the body of water with the SV.

The details of one or more implementations of the present disclosure are set forth in the accompanying drawings and the description that follows. Other features, objects, and advantages of the present disclosure will be apparent from the description and drawings, and from the claims.

DETAILED DESCRIPTION

For the purposes of promoting an understanding of the principles of the present disclosure, reference will now be made to the implementations illustrated in the drawings, and specific language will be used to describe the same. Nevertheless, no limitation of the scope of the disclosure is intended. Any alterations and further modifications to the described devices, systems, methods, and any further application of the principles of the present disclosure are fully contemplated as would normally occur to one skilled in the art to which the disclosure relates. In particular, it is fully contemplated that the features, components, steps, or a combination of these described with respect to one implementation may be combined with the features, components, steps, or a combination of these described with respect to other implementations of the present disclosure.

The present disclosure is directed to systems, methods, and apparatuses for detecting fluids in water, such as sea water, ocean water, or fresh water, and collecting the detected fluids. Fluids, such as oil, drilling mud, other drilling fluids (for example, completion fluids or other treatment fluids mixed with drilling mud), chemicals used in hydrocarbon exploration or production (such as oil exploration or production), contaminated water, and other types of fluids, may be expelled or otherwise released during a hydrocarbon exploration or production operation. For example, fluids may be expelled during a flaring operation on an offshore platform, or fluids may be released as a result of a leak, such as a leak in equipment, such as a pipeline, associated with the operations of an offshore platform. For example, during a flaring operation, a volume of fluid, such as oil, may be released into the water. The released fluid is detected in the water and collected.

In some implementations, a system for detecting and collecting released fluids includes one or more submersible vehicles (SVs). In some implementations, the SV may be a remotely operated vehicle (ROVs), such as a seafloor science ROV (SSROV), that is operable to autonomously search for and identify a released fluid within water. Other types of SVs may include work-class ROVs, heavy work-class ROVs, and autonomous ROVs. An SV or team of SVs are stationed at, introduced into, or directed to an area where a fluid release into water has occurred or is predicted to occur. In some instances, the SV or team of SVs may be introduced into or directed to an area where a released fluid is believed to be present. Upon reaching a designated location, the SV or team of SVs search the designated location for the presence of a released fluid. Where a team of SVs are used, the SVs may work as a team to locate and remediate the released fluid. For example, in some implementations, the SV or team of SVs may systematically search an area of the designated location to identify the presence of a released fluid. In some instances, the SV or team of SVs may systematically search an area according to a virtual three-dimensional (3D) grid established within the area. In some implementations, where multiple SVs are present, the SVs may search along different portions of the area along the established 3D grid. Thus, the area may be searched in a shorter period of time compared to a search performed by a single or fewer number of SVs. The 3D grid may be defined with respect to a desired coordinate system, such as a Cartesian coordinate system, a polar coordinate system, a cylindrical coordinate system, or a spherical coordinate system.

An SV within the scope of the present disclosure includes one or more sensors operable to measure rheological properties of fluids and use these measurements to detect the presence of a released fluid. In some implementations, an SV operates autonomously to detect rheological properties to detect the presence of a released fluid. Sensors such as resonator sensors, microcapillary resonators, thin-film bulk acoustic wave resonators, micro-electro mechanical systems (MEMS), or other types of sensors may be used to detect and measure rheological properties. For example, in some implementations, an SV may be operable to detect fluid viscosity, fluid density, and temperature of a fluid. In other implementations, an SV may be operable to measure additional, fewer, or different rheological properties to detect a released fluid. A fluid type within water may be determinable based, for example, on a measured density and viscosity. Temperature measurements may also be used to detect released fluids, because the released fluids may have different conductivity than the surrounding water. As result, the released fluids may have a different temperature within the water. Further, at the time of release, an initial temperature of the released fluid may be higher or lower than the surrounding water. Therefore, the SV may be operable to detect the presence of released fluids within the water, especially when the measurements are made proximate to the time the fluids are released into the water. Temperature sensors may also be used by the SVs to detect hazards, such as fires, so that the SVs can avoid those areas.

In some implementations, a fluid type is determined by comparing measured rheological properties to rheological properties of known fluids. For example, the measured rheological properties may be compared to a database containing rheological properties of known fluids. Once a match is made, the type of fluid encountered by the SV is determined. In some implementations, the fluid type determination may be performed on board of the SV. For example, the SV may include a computer of a type described in more detail later. The computer may include memory containing a database of fluid types and their associated rheological properties. A processor of the computer may receive rheological data sensed by sensors onboard of the SV, directly or indirectly, and compare the received rheological data to the rheological properties of the fluid types stored in memory. In other implementations, the fluid type determination may be performed remotely from the SV. For example, the SV may transmit the sensed rheological data to a ship or oil platform where the comparison takes place. The outcome of the comparison may be received by the SV. The SV operates in response to the received information.

When a fluid type is identified, whether remotely or onboard of the SV, the SV responds accordingly. For example, if a preselected fluid type is detected, the SV operates to collect the detected fluid, as described in more detail later. In some implementations, the SV reacts autonomously to the identification of a released fluid to begin collection of the released fluid. If a fluid type other than a preselected fluid type is identified, the SV responds by continuing to search for preselected fluid types. In this way, the SV is operable to identify and differentiate different fluid types, such as a hydrocarbon, a drilling fluid (such as a drilling mud), or other types of chemicals. In response, to the identification, the SV reacts in accordance with whether the detected fluid is one of a preselected type of fluid or not.

In some implementations, an SV may be remotely operated, such as by a user located remotely, to begin collection of a released fluid. The user may control operation of the SV, including movement of the SV and when a collection system of the SV is operated. Remote operation may be used, for example, when collected rheological information is incomplete or the SV is unable to identify a released fluid based on the collected rheological information. In still other implementations, where the collected rheological information is unable to be fully matched to a fluid type, the SV may be programmed to react in predefined way notwithstanding the incomplete information. For example, the collected rheological information may include an identifiable viscosity or the detected viscosity may be outside of a range of viscosity values associated with a preselected released fluid. In such case, the SV may be programmed to proceed in collecting the fluid notwithstanding the incomplete rheological information.

Figure 1:
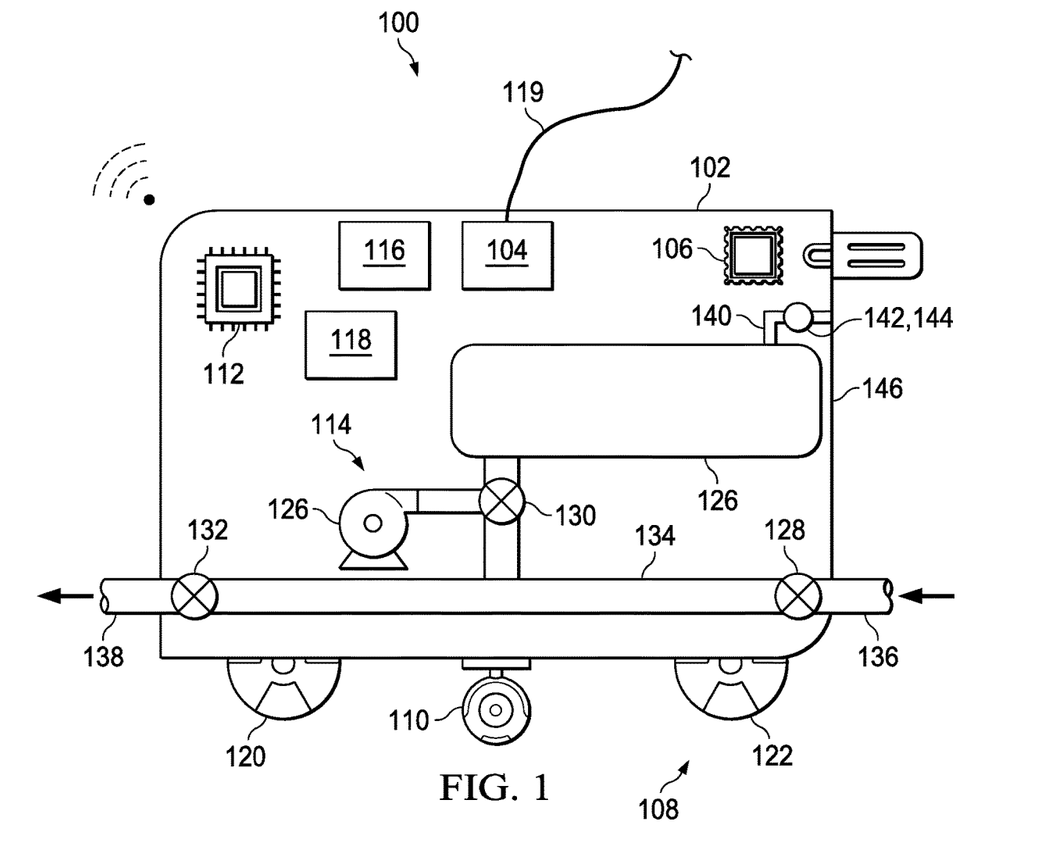
FIG. 1 is a schematic view of an example submersible vehicle (SV), according to some implementations of the present disclosure.

FIG. 1 is a schematic of an example SV 100 within the scope of the present disclosure. The SV 100 includes a housing 102 that houses a power supply 104, sensors 106, a propulsion system 108, a camera 110, a global position system (GPS) receiver 112, a fluid collection system 114, a computer 116, a communication system 118, and an umbilical cable 119. The sensors 106 are operable to sense rheological fluid properties. The GPS receiver 112 is operable to determine a global position of the SV 100, including a depth below a water surface of the SV 100. In some implementations, the SV 100 may be operable up to 100 meters below the surface of the water. In other implementations, the SV 100 may be operable at depths greater than 100 meters. The camera 110 provides images of an environment adjacent the SV 100. In some implementations, the camera 110 may be operable to provide still images, video images, or both, of the environment. In some implementations, the camera 110 may be operable to provide real-time images, whether still images or video images or both. The images captured by the camera 110 may be transmitted to a remote location, used by the computer 116 to control an operation of the SV 100, or both. For example, the SV 100 may use one or more images from the camera 110 to detect an object near the SV 100, such as a volume of released fluid or another SV. If an object is detected using the video images, the SV 100, for example, may alter a course of travel, such as to avoid collision with the detected object, or steer into the object, such as where the object is determined to be a volume of released fluid.

The computer 116 controls operations of the SV 100. For example, the computer 116 may use information obtained by the GPS receiver 112, stored information, or both, to determine a position of the SV 100 and navigate a course to be traveled by the SV 100. As explained earlier, the computer 116 may use the sensors 106 to detect the presence of a preselected fluid type and respond by collecting the detected fluid if the detected fluid is one of the preselected fluid types. The computer 116 controls travel of the SV 100 using the propulsion system 108. For example, the computer 116 may operate the propulsion system 108 to propel and direct the SV 100 along a predetermined course established and tracked using, for example, data obtained via the GPS receiver 112. In the illustrated example, the propulsion system 108 includes two propulsion devices 120 and 122. However, in other implementations, the propulsion system 108 may include any number of propulsion devices. In some implementations, the propulsion devices 120 and 122 include a motor attached to and operable to rotate a propeller. The propulsion devices 120 and 122 may be independently operated, for example, to change an orientation, a direction of travel, a speed of travel, or a combination of these of the SV 100.

The computer 116 may use the video images from the camera 110 to detect a foreign object and react accordingly, such as to change a course of travel to avoid collision with the detected object. The computer 116 also operates the fluid collection system 114 when a preselected fluid type is detected. Furthermore, the computer 116 is operable to control movement of the SV 100 and operation of the fluid collection system 114 of the SV 100 to ensure collection of the released fluid.

In the illustrated example of FIG. 1, the fluid collection system 114 includes a storage tank 124, a fluid pump 126, a first valve 128, a second valve 130, a third valve 132, a piping system 134, an inlet 136, and an outlet 138. The illustrated configuration and components of the fluid collection system 114 are provided merely as an example. The present disclosure encompasses a fluid collection systems having additional, fewer, or different components arranged in a similar or different configuration.

The first valve 128 and the third valve 132 may be in a closed configuration when the fluid collection system 114 is in an off condition. With the first and third valves 128 and 132 in the closed configuration, water or other fluids are prevented from entering the piping system 134 and, thus, kept out of the fluid collection system 114. When the fluid collection system 114 is activated, such as when a released fluid is detected, the first valve 128 is opened and the pump 126 is activated to generate a fluid flow from the inlet 136 to the storage tank 124. Any initial fluid within the storage tank 124, such as air, is vented via a vent 140. A fourth valve 142 coupled to the vent 140 opens upon activation of the fluid collection system 114 such that the initial fluid within the storage tank 124 is expelled as the released fluid is collected. In some implementations, the vent 140 may include a sensor 144 operable to distinguish the initial fluid contained in the storage tank 124 from a fluid being collected. When the sensor 144 detects the released fluid, the computer 116 may close the fourth valve 142 and cease operation of the pump 126. Detection of the released fluid by the sensor 144 may indicate that the storage tank 124 is full of the released fluid. In other instances, an orientation of the SV 100 may result in detection of the released fluid by the sensor 144 even when the storage tank 124 is not fully filled with the released fluid. In other implementations, the pump 126 may be configured to vent or otherwise discharge fluid contained in the tank 124 as released fluid is being collected.

The fluid collection system 114 may operate to collect released fluid for so long as released fluid remains in the water or until the storage tank 124 is filled. During operation of the fluid collection system 114, the sensors 106 may continue to operate to detect released fluid within the water. Thus, operating to detect a released fluid with the sensors 106 may be performed in real-time during fluid collection by the SV 100. In some implementations, when the sensors 106 no longer detect released fluid, the fluid collection system 114 may cease operation. For example, the computer 116 may detect the absence of released fluid based on data received from the sensors 106. In response, the computer 116 may stop operation of the fluid pump 126 and close the first valve 128 and fourth valve 142. As shown in FIG. 1, the sensors 106 and the inlet 136 are located on a common side 146 of the SV 100. As a result, the sensors 106 sense for the presence of released fluid on the same side of the SV 100 from where the released fluid is to be captured by the inlet 136 of the fluid collection system 114.

Fluid contained in the storage tank 124 may be removed, for example, by opening the third valve 132 and fourth valve 142 and operating the fluid pump 126 in reverse. As a result, the contents of the storage tank 124 are expelled through the outlet 138. In some implementations, a conduit, such as a pipe, may be coupled to the outlet 138 when the contents of the storage tank 124 are removed. Thus, in some implementations, the SV 100 may remain in the water while the contents of the storage tank 124 are emptied. In addition to detecting and capturing released fluids, the SV 100 may be used to perform offshore maintenance and underwater surveying and inspection.

In other implementations, the SV 100 may bypass or omit the storage tank 124 and transfer collected released fluid directly to an external storage tank. Use of external tanks provides for continuous and uninterrupted fluid recovery. An external storage tank may be coupled to the SV 100, such as to the outlet 138 via a conduit. The conduit may be flexible and have a length that permits the SV 100 to patrol a preselected area and collect released fluids in that preselected area. In some implementations, the external storage tank is provided at the surface of the water. For example, in some implementations, the storage tank may be a stand-alone tank. In other implementations, the storage tank may be attached to or form part of another structure at the surface, such as a ship or other vessel. Further, the storage tank may be a buoyant tank located at or near the surface of the water.

When the SV 100 detects a released fluid in the water, the SV 100 may operate the propulsion system 108 to position and orient the SV 100 to collect the released fluid. In implementations in which a plurality of SVs 100 are working together to capture released fluid, each SV 100 may work autonomously, as a part of a collective in which each SV 100 is operated according to a plan or design to efficiently collect the released fluid, or one or more of the SVs 100 may be manually operated by a remote operator. During a fluid recover operation involving a plurality of SVs 100 working collectively, a computer 116 of one of the SVs 100 or a remotely located computer may obtain position information of each of the SVs 100 as well as one or more locations of the detected released fluid and control the position, movement, orientation, and operation (such as operation of the fluid collection system 114) of the SVs 100 to efficiently collect the released fluid. In still other implementations, the computer 116 of each SV 100 may receive operating information, such as position information, of the other SVs 100, and each of the SVs 100 may be operable to recover released fluid autonomously, in concert, while, for example, avoiding collisions with other SVs 100 and while avoiding areas in which a released fluid has already been serviced by another SV 100. This collective control of the plurality of SVs 100 may include controlling movement of the SVs 100 to avoid collision between SVs 100 during a search for or recovery of a released fluid.

In some implementations, one or more SVs 100 may be located at different selected depths within the water and follow preprogrammed paths at the selected depths. For example, preprogrammed paths may be paths oriented relative to a grid virtually established in the water. In some implementations, one or more of the SVs 100 may operate in a circular fashion, such that an SV 100 circles a released fluid in the water. In some instances, the SV 100 may circle the released fluid with consecutive circles having changing radiuses. In other implementations, one or more SVs 100 may be located at different depths and move back and forth along adjacent lines to collect released fluids. These operating schemes are provided merely as examples, and, as such, other operating schemes are within the scope of the present disclosure.

In some implementations, the computer of one SV may be operable to control a plurality of SVs. For example, an SV may control one or more operations of one or more other SVs. Control by one SV of one or more additional SVs may occur, for example, during movement of SVs along a virtual grid established in a volume of water during a search for released fluid and during collection of a released fluid.

Communications between SVs or between an SV and a remote location or both is performed using the communications system 118. In some implementations, the communications system 118 is separate from the computer 116. In other implementations, the communications system 118 forms part of the computer 116. The SV 100 uses the communication to send and receive information. Information sent or received by communications system 118 may include sensor data, propulsion data, control information (such as control information sent from one SV to another or from a remote location to an SV), image data obtained from the camera 110, a status of an SV, or other desired information. In still other implementations, the SV 100 may include functionality such that the SV 100 is capable of being remotely controlled.

The communications system 118 is coupled to the umbilical cable 119. Information is sent from or received by the SV 100 via the umbilical cable 119. Information from the SV 100 may be transmitted to or received from a remote location via the umbilical cable 119. Further, in some implementations, communications sent through the umbilical cable 119 may ultimately be routed to one or more other SVs via a counterpart umbilical cable of those SVs or wirelessly. In still other implementations, the umbilical cable 119 may be omitted so that the SV 100 is untethered. In implementations that omit an umbilical cable, communications between the SV 100 and a remote location, between one or more other SVs, or both may be accomplished via wireless communications.

The power supply 104 stores energy for use by the various systems and components of the SV 100. In some implementations, the power supply 104 includes one or more batteries to provide electrical power to the SV 100. In some implementations, the SV 100 may receive electrical power via the umbilical cable 119. Thus, in some implementations in which the SV 100 receives electrical power via the umbilical cable 119, the power supply 104 may be a backup power supply or the power supply 104 may be omitted.

Figure 2:
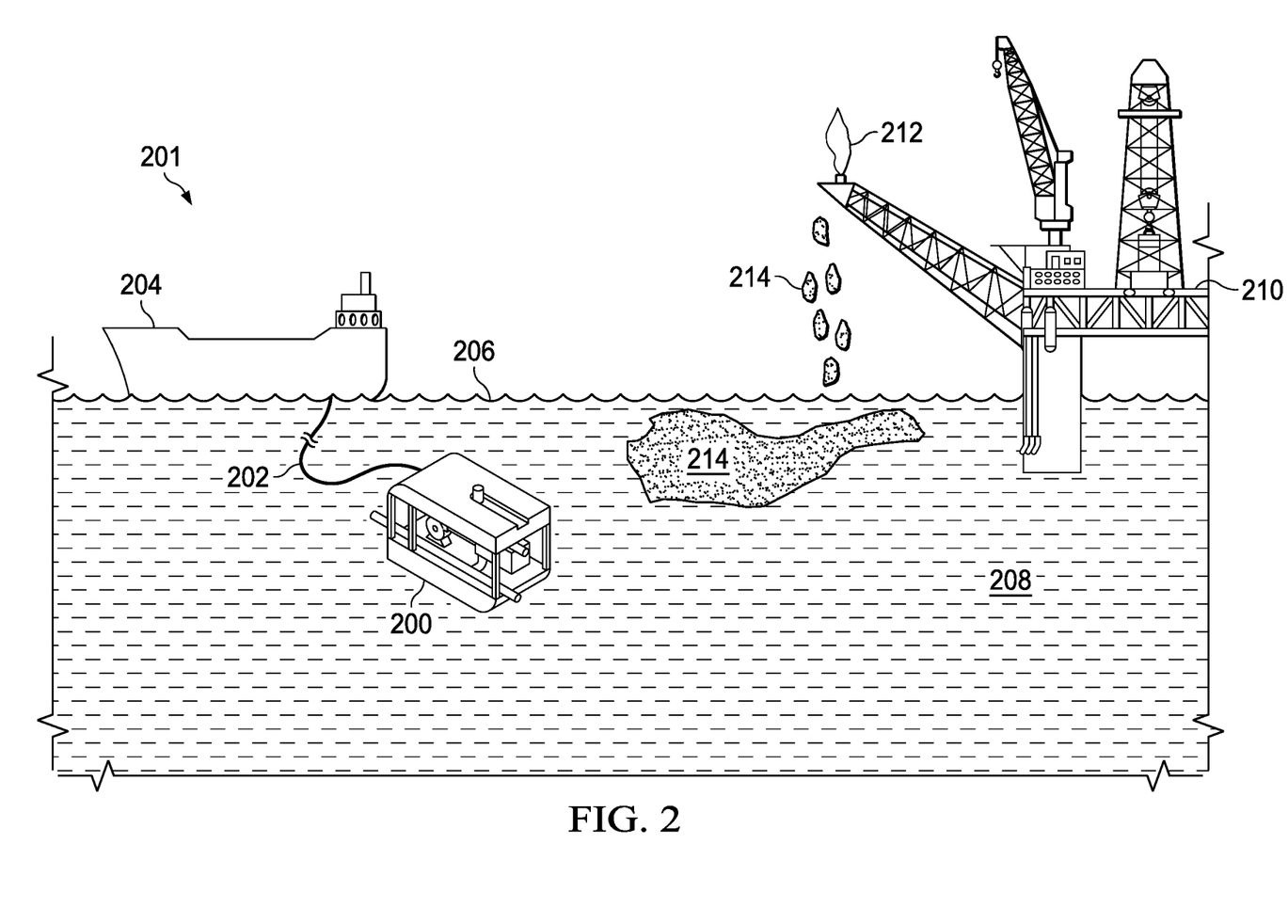
FIG. 2 is a schematic view of an example recovery system for recovering a fluid released into a body of water, according to some implementations of the present disclosure.

FIG. 2 is a schematic view of a recovery system 201 that includes an SV 200 tethered via an umbilical cord 202 to a ship or other vessel 204 at the surface 206 of a body of water 208. In other implementations, the SV 200 may be untethered. Although a single SV 200 is shown, it is understood that a plurality of SVs 200 may be present. Further, in some implementations, multiple SVs 200 may operate in concert with each other to detect and to collect released fluids 214 within the water 208. An oil platform 210 is located at the surface 206. Although an oil platform 210 is illustrated, the scope of the disclosure is not so limited. Rather, other types of water-based structures are encompassed, such as a jack up rig or a drillship. Still further, SVs within the scope of the disclosure may be used to detect and recover released fluids associated with other equipment, such as offshore barge production facilities and underwater pipelines. As shown, the oil platform 210 is undergoing a flaring operation, producing a flare 212 and expelling a released fluid 214, such as oil. Other types of fluid are within the scope of the disclosure, such as those described earlier.

In some implementations, one or more SVs 200 may be placed into operation in the water 208, such as in an area where a released fluid would be expected to enter the water during a flaring operation, and be actively searching for released fluid prior to the start of the flaring operation. In other implementations, one or more SVs 200 may be inserted into the water or operated to begin searching for released fluids, or both, at any time before, during, or after a flaring operation or another operation in which a fluid release may be anticipated.

The SV 200 shown in FIG. 2 is in the process of searching for released fluid 214. In this example, the SV 200 contains an internal storage tank for collecting the released fluid 214. SVs 200 having internal storage tanks may be used in circumstances in which an amount of released fluid 214 is anticipated to be of a volume that can be recovered by one or more SVs 200 without additional remote storage capacity.

Figure 3:
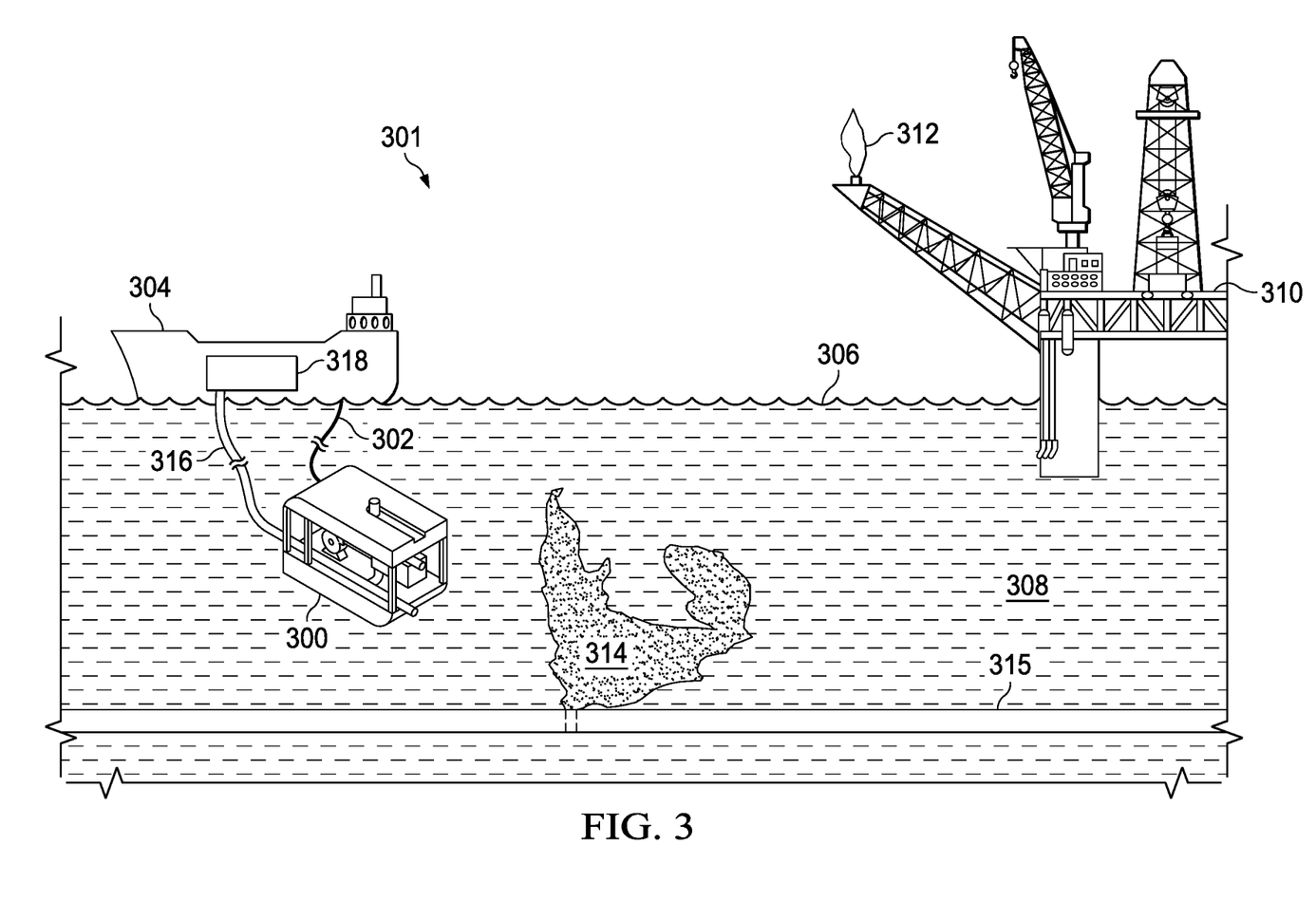
FIG. 3 is a schematic view of another example recovery system for recovering a fluid released into a body of water, according to some implementations of the present disclosure.

FIG. 3 is a schematic view of a recovery system 301 that includes an SV 300 tethered via an umbilical cord 302 to a ship or other vessel 304 at the surface 306 of a body of water 308. An oil platform 310 is located at the surface 306. In other implementations, types of oil production or processing equipment other than or in addition to the oil platform 310 may be may be present. As shown, a released fluid 314, such as a liquid hydrocarbon, is present in the water 308 as a result of a leak in a submerged pipeline 315. Other types of fluid are within the scope of the disclosure, such as those described earlier.

Although a single SV 300 is shown, it is understood that a plurality of SVs 300 may be present. Furthermore, in some implementations, multiple SVs 300 may operate in concert with each other to collect released fluids 314 within the water 308. As explained earlier, in some implementations, the SV 300 may be untethered such that the SV 300 operates using an onboard power supply and communicates wirelessly. The SV 300 is also coupled to the vessel 304 via a conduit 316 such that a fluid collection system of the SV 300 is operable to transfer the released fluid 314 that is collected to external storage tanks 318 contained in, on, or within the vessel 304. In some implementations, the external storage tanks 318 may be separate from the vessel 304 and may be located at or near the surface 306. The use of external storage tanks 318 allows for the one or more SVs 300 to operate for longer periods of time without having to offload released fluids 314 collected in an internal storage tank onboard of the SV 300. Further, with electrical power provided via the umbilical cable 302, the SV 300 may be able to operate indefinitely where the collected released fluid 314 is conducted to external storage tanks 318 via the conduit 316.

Systems within the scope of the present disclosure, such as recovery systems 201 and 301, operate to collect fluids released into a body of water during a hydrocarbon exploration or production operation. By collecting released fluids, environmental impact is reduced or eliminated because the released fluids are removed from the water. Further, the collected fluids may be reused, thereby avoiding the cost associated with obtaining additional quantities of these fluids. Costs for conventional remediation activities are also avoided. For example, in a case where the released fluid is oil, the oil may be captured and processed, thereby increasing production efficiency. Further, the systems avoid the use of other chemicals presently used to remediate inadvertent releases of fluids during hydrocarbon exploration or production. For example, presently, other chemicals, such as environmentally-friendly soaps, may be used on spills or other inadvertent releases of oil. The soaps assist in breaking down the oil in order to reduce harmful environmental effects. The systems described avoid the cost associated with deploying these remediation chemicals and any associated harmful environmental effects.

Further, the described systems avoid spread of released fluid. For example, where one or more SVs are prepositioned in the water prior to an operation that has the potential for releasing fluid or shortly after fluid release, the SVs operate to recapture the released fluid, thereby preventing the released fluid from spreading. Thus, the system of the present disclosure contain released fluids to confined area and collect the released fluid to reduce environmental impact. Although the recovery systems 201 and 301 are shown in the context of an oil platform, the systems are also applicable to collecting released fluids from leaks in a pipeline or at other productions, processing, or transportation equipment.

Figure 4:
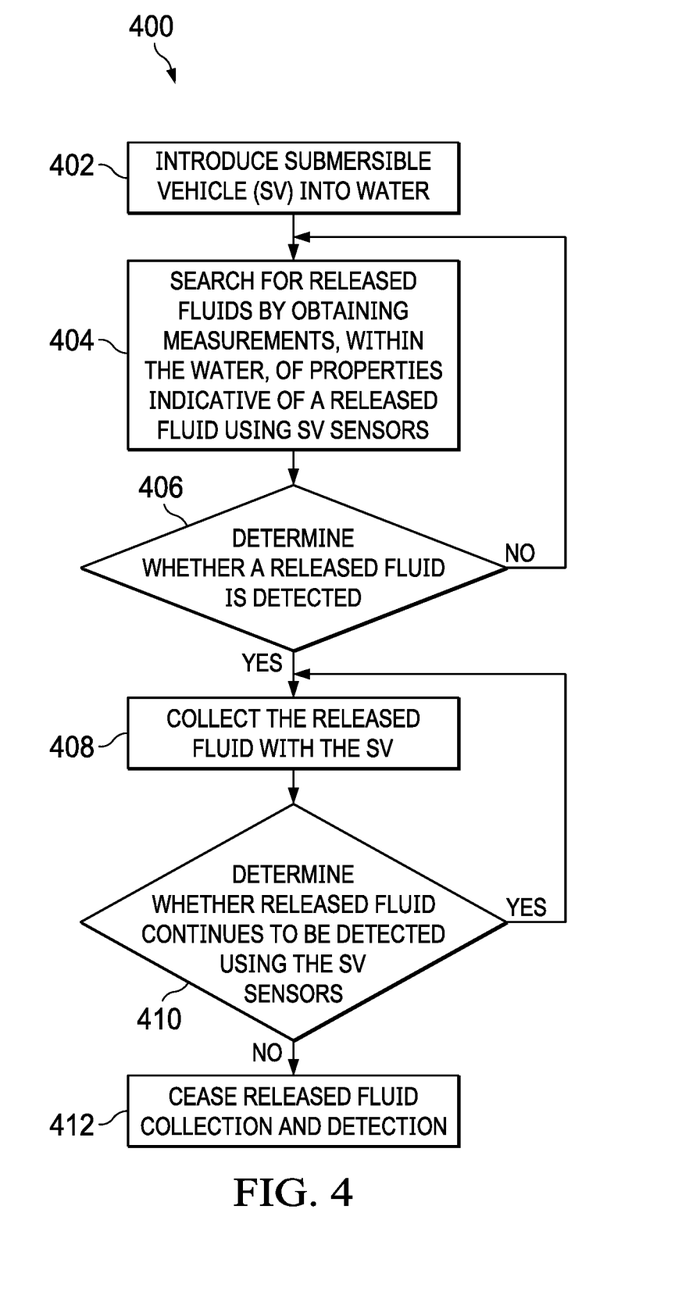
FIG. 4 is a flowchart of an example method for remediating fluid released into a body of water during the course of a petroleum exploration or production operation, according to some implementations of the present disclosure.

FIG. 4 is a flowchart of an example method 400 for remediating fluid released into a body of water during the course of a petroleum exploration or production operation. Although the method 400 is described in the context of a single SV, it is understood that the method 400 may involve the use of multiple SVs. At 402, an SV is introduced into water. The SV may be introduced into the water at or near a location where a fluid may be released. In some implementations, the SV may be introduced into the water prior to an operation, such as a petroleum exploration or production operation, that may involve a fluid release into the water. At 404, the SV takes measurements within the water in an effort to detect a released fluid within the water. For example, the SV senses fluid rheological properties. The sensed rheological properties are compared to a predefined list of rheological properties that are associated with types of possible released fluids. For example, sensors on the SV may detect rheological properties, such as viscosity and density, to determine the presence of a released fluid. Other sensors, such temperature sensors, may also be used to detect the presence of a released fluid. At 406, if a match is determined, a type of released fluid is identified, and the method continues to 408 where the SV proceeds to collect the released fluid. If a predetermined type of released fluid is not detected based on the sensed rheological properties, the SV continues to search for released fluids.

At 408, when a released fluid is detected, the SV operates to collect the released fluid. In some implementations, the SV may collect the released fluid in a storage tank onboard of the SV. In other implementations, the SV may conduct recovered released fluid to a remote storage tank, such as an external storage tank located at or near the surface of the water. The external storage tank may be a standalone storage tank or may form part of another structure, such as a ship. The SV may be directed along a predetermined course to ensure recovery of the released fluid. For example, the SV may move in consecutive circles having different radiuses at a particular depth. As explained earlier, the SV may be operated according to other types of predetermined courses. As also explained earlier, multiple SVs may be used and operated in concert to collect the released fluid. At 410, the SV operates to collect the released fluid until, for example, the released fluid is no longer detected. For example, the SV may cease collecting the released fluid when the sensors of the SV are no longer able to detect the released fluid in the water. Thus, if the SV continues to detect the released fluid based, for example, based on sensed rheological properties, the SV continues collection of the released fluid. If the released fluid is no longer detected, the SV ceases collection activities. In some implementations, the SV may return to a fluid detection mode when a released fluid is no longer detected. In other implementations, the SV may cease fluid collection and fluid detection activities when a released fluid is no longer detected, as indicated at 412.

Figure 5:
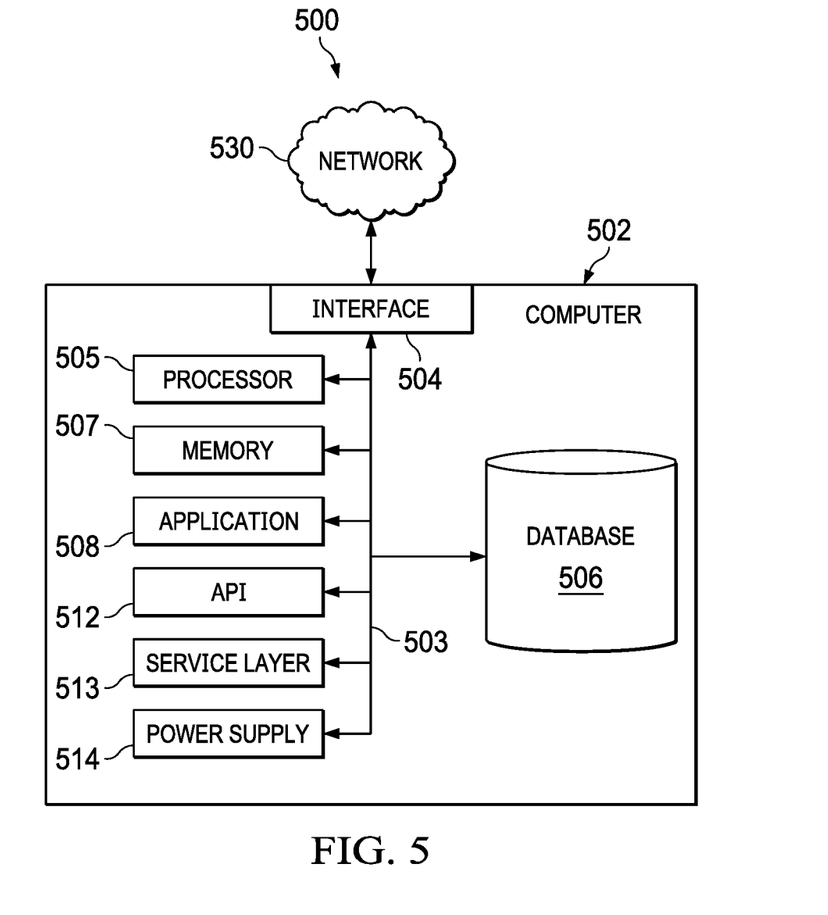
FIG. 5 is a block diagram illustrating an example computer system used to provide computational functionalities associated with described algorithms, methods, functions, processes, flows, and procedures as described in the present disclosure, according to some implementations of the present disclosure.

FIG. 5 is a block diagram of an example computer system 500 used to provide computational functionalities associated with described algorithms, methods, functions, processes, flows, and procedures described in the present disclosure, according to some implementations of the present disclosure. The illustrated computer 502 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 502 can include input devices such as keypads, keyboards, and touch screens that can accept user information. Also, the computer 502 can include output devices that can convey information associated with the operation of the computer 502. The information can include digital data, visual data, audio information, or a combination of information. The information can be presented in a graphical user interface (UI) (or GUI).

The computer 502 can serve in a role as a client, a network component, a server, a database, a persistency, or components of a computer system for performing the subject matter described in the present disclosure. The illustrated computer 502 is communicably coupled with a network 530. In some implementations, one or more components of the computer 502 can be configured to operate within different environments, including cloud-computing-based environments, local environments, global environments, and combinations of environments.

At a high level, the computer 502 is an electronic computing device operable to receive, transmit, process, store, and manage data and information associated with the described subject matter. According to some implementations, the computer 502 can also include, or be communicably coupled with, an application server, an email server, a web server, a caching server, a streaming data server, or a combination of servers.

The computer 502 can receive requests over network 530 from a client application (for example, executing on another computer 502). The computer 502 can respond to the received requests by processing the received requests using software applications. Requests can also be sent to the computer 502 from internal users (for example, from a command console), external (or third) parties, automated applications, entities, individuals, systems, and computers.

Each of the components of the computer 502 can communicate using a system bus 503. In some implementations, any or all of the components of the computer 502, including hardware or software components, can interface with each other or the interface 504 (or a combination of both), over the system bus 503. Interfaces can use an application programming interface (API) 512, a service layer 513, or a combination of the API 512 and service layer 513. The API 512 can include specifications for routines, data structures, and object classes. The API 512 can be either computer-language independent or dependent. The API 512 can refer to a complete interface, a single function, or a set of APIs.

The service layer 513 can provide software services to the computer 502 and other components (whether illustrated or not) that are communicably coupled to the computer 502. The functionality of the computer 502 can be accessible for all service consumers using this service layer. Software services, such as those provided by the service layer 513, can provide reusable, defined functionalities through a defined interface. For example, the interface can be software written in JAVA, C++, or a language providing data in extensible markup language (XML) format. While illustrated as an integrated component of the computer 502, in alternative implementations, the API 512 or the service layer 513 can be stand-alone components in relation to other components of the computer 502 and other components communicably coupled to the computer 502. Moreover, any or all parts of the API 512 or the service layer 513 can be implemented as child or sub-modules of another software module, enterprise application, or hardware module without departing from the scope of the present disclosure.

The computer 502 includes an interface 504. Although illustrated as a single interface 504 in FIG. 5, two or more interfaces 504 can be used according to particular needs, desires, or particular implementations of the computer 502 and the described functionality. The interface 504 can be used by the computer 502 for communicating with other systems that are connected to the network 530 (whether illustrated or not) in a distributed environment. Generally, the interface 504 can include, or be implemented using, logic encoded in software or hardware (or a combination of software and hardware) operable to communicate with the network 530. More specifically, the interface 504 can include software supporting one or more communication protocols associated with communications. As such, the network 530 or the interface's hardware can be operable to communicate physical signals within and outside of the illustrated computer 502.

The computer 502 includes a processor 505. Although illustrated as a single processor 505 in FIG. 5, two or more processors 505 can be used according to particular needs, desires, or particular implementations of the computer 502 and the described functionality. Generally, the processor 505 can execute instructions and can manipulate data to perform the operations of the computer 502, including operations using algorithms, methods, functions, processes, flows, and procedures as described in the present disclosure.

The computer 502 also includes a database 506 that can hold data for the computer 502 and other components connected to the network 530 (whether illustrated or not). For example, database 506 can be an in-memory, conventional, or a database storing data consistent with the present disclosure. In some implementations, database 506 can be a combination of two or more different database types (for example, hybrid in-memory and conventional databases) according to particular needs, desires, or particular implementations of the computer 502 and the described functionality. Although illustrated as a single database 506 in FIG. 5, two or more databases (of the same, different, or combination of types) can be used according to particular needs, desires, or particular implementations of the computer 502 and the described functionality. While database 506 is illustrated as an internal component of the computer 502, in alternative implementations, database 506 can be external to the computer 502.

The computer 502 also includes a memory 507 that can hold data for the computer 502 or a combination of components connected to the network 530 (whether illustrated or not). Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 5, two or more memories 507 (of the same, different, or combination of types) can be used according to particular needs, desires, or particular implementations of the computer 502 and the described functionality. While memory 507 is illustrated as an internal component of the computer 502, in alternative implementations, memory 507 can be external to the computer 502.

The application 508 can be an algorithmic software engine providing functionality according to particular needs, desires, or particular implementations of the computer 502 and the described functionality. For example, application 508 can serve as one or more components, modules, or applications. Further, although illustrated as a single application 508, the application 508 can be implemented as multiple applications 508 on the computer 502. In addition, although illustrated as internal to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion and management circuits, including recharging, standby, and power management functionalities. In some implementations, the power-supply 514 can include a power plug to allow the computer 502 to be plugged into a wall socket or a power source to, for example, power the computer 502 or recharge a rechargeable battery.

There can be any number of computers 502 associated with, or external to, a computer system containing computer 502, with each computer 502 communicating over network 530. Further, the terms "client," "user," and other appropriate terminology can be used interchangeably, as appropriate, without departing from the scope of the present disclosure. Moreover, the present disclosure contemplates that many users can use one computer 502 and one user can use multiple computers 502.

Described implementations of the subject matter can include one or more features, alone or in combination.

For example, in a first implementation, a computer-implemented method, including detecting the presence of a released fluid in a body of water with a submersible vehicle (SV) and collecting a detected released fluid in the body of water with the SV.

The foregoing and other described implementations can each, optionally, include one or more of the following features:

A first feature, combinable with any of the following features, the method further including introducing the SV into the body of water prior to release of the released fluid.

A second feature, combinable with any of the previous or following features, wherein detecting the presence of a released fluid in a body of water with an SV includes sensing rheological properties of the released fluid with one or more sensors of the SV.

A third feature, combinable with any of the previous or following features, wherein collecting a detected released fluid in the body of water with the SV includes activating a fluid collection system of the SV.

A fourth feature, combinable with any of the previous or following features, wherein collecting a detected released fluid in the body of water with the SV includes collecting the detected released fluid in storage tank onboard of the SV or in an external tank that is external of the SV.

A fifth feature, combinable with any of the previous or following features, wherein detecting the presence of a released fluid in a body of water includes comparing rheological properties sensed with one or more sensors of the SV to a database of rheological properties associated with known fluids and identifying the released fluid as one of the known fluids whose rheological properties correspond to the sensed rheological properties.

A sixth feature, combinable with any of the previous or following features, wherein detecting the presence of a released fluid in a body of water with a submersible vehicle (SV) includes detecting the presence of the released fluid in the body of water with a plurality of SVs operating in concert with each other.

A seventh features, combinable with any of the previous features, the method further including sensing for the presence of the released fluid while collecting the detected released fluid in the body of water with the SV.

In a second implementation, a non-transitory, computer-readable medium storing one or more instructions executable by a computer system to perform operations including detecting the presence of a released fluid in a body of water with a submersible vehicle (SV) and collecting a detected released fluid in the body of water with the SV.

The foregoing and other described implementations can each, optionally, include one or more of the following features:

A first feature, combinable with any of the following features, the method further including introducing the SV into the body of water prior to release of the released fluid.

A second features, combinable with any of the previous or following features, wherein detecting the presence of a released fluid in a body of water with an SV includes sensing rheological properties of the released fluid with one or more sensors of the SV.

A third feature, combinable with any of the previous or following features, wherein collecting a detected released fluid in the body of water with the SV includes activating a fluid collection system of the SV.

A fourth feature, combinable with any of the previous or following features, wherein collecting a detected released fluid in the body of water with the SV includes collecting the detected released fluid in storage tank onboard of the SV or in an external tank that is external of the SV.

A fifth feature, combinable with any of the previous or following features, wherein detecting the presence of a released fluid in a body of water includes comparing rheological properties sensed with one or more sensors of the SV to a database of rheological properties associated with known fluids and identifying the released fluid as one of the known fluids whose rheological properties correspond to the sensed rheological properties.

A sixth feature, combinable with any of the previous or following features, wherein detecting the presence of a released fluid in a body of water with a submersible vehicle (SV) includes detecting the presence of the released fluid in the body of water with a plurality of SVs operating in concert with each other.

A seventh feature, combinable with any of the previous features, the one or more instructions further including sensing for the presence of the released fluid while collecting the detected released fluid in the body of water with the SV In a third implementation, a computer-implemented system, including one or more processors and a non-transitory computer-readable storage medium coupled to the one or more processors and storing programming instructions for execution by the one or more processors, the programming instructions instructing the one or more processors to detect the presence of a released fluid in a body of water with a submersible vehicle (SV) and collect a detected released fluid in the body of water with the SV.

The foregoing and other described implementations can each, optionally, include one or more of the following features:

A first feature, combinable with any of the following features, wherein the one or more programming instructions further includes programming instructions operable to instruct the one or more processors to introduce the SV into the body of water prior to release of the released fluid.

A second feature, combinable with any of the previous or following features, wherein the programming instructions operable to instruct the one or more processors to detect the presence of a released fluid in a body of water with an SV includes programming instructions operable to instruct the one or more processors to sense rheological properties of the released fluid with one or more sensors of the SV.

A third feature, combinable with any of the previous or following features, wherein the programming instructions operable to instruct the one or more processors to collect a detected released fluid in the body of water with the SV includes programming instructions to instruct the one or more processors to activate a fluid collection system of the SV.

A fourth feature, combinable with any of the previous or following features, wherein the programming instructions operable to instruct the one or more processors to collect a detected released fluid in the body of water with the SV includes programming instructions operable to instruct the one or more processors to collect the detected released fluid in storage tank onboard of the SV or in an external tank that is external of the SV. A fifth feature, combinable with any of the previous or following features, the programming instructions operable to instruct the one or more processors to detect the presence of a released fluid in a body of water includes programming instructions operable to instruct the one or more processors to compare rheological properties sensed with one or more sensors of the SV to a database of rheological properties associated with known fluids and identify the released fluid as one of the known fluids whose rheological properties correspond to the sensed rheological properties.

A sixth feature, combinable with any of the previous or following features, wherein the programming instructions operable to instruct the one or more processors to detect the presence of a released fluid in a body of water with a submersible vehicle (SV) includes programming instructions operable to instruct the one or more processors to detect the presence of the released fluid in the body of water with a plurality of SVs operating in concert with each other.

A seventh feature, combinable with any of the previous features, the programming instructions further including programming instructions operable to instruct the one or more processors to sense for the presence of the released fluid while collecting the detected released fluid in the body of water with the SV.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as standalone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/nonvolatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of the present disclosure have been described. Nevertheless, it will be understood that various modifications may be made without departing from the spirit and scope of the present disclosure. Accordingly, other embodiments are within the scope of the following claims.

What is claimed is:

1. A method for detecting a presence of a released fluid in a body of water and collecting the released fluid from the body of water, the released fluid released from a petroleum operation, the method comprising:

detecting the presence of the released fluid in the body of water with a submersible vehicle;

based on detecting the presence of the released fluid, operating a fluid collection system of the submersible vehicle to collect the released fluid into an internal storage tank of the submersible vehicle; and transferring the released fluid from the internal storage tank of the submersible vehicle to an external storage tank on a surface of the body of water via a conduit.

2. The method of claim 1, further comprising, before detecting the presence of the released fluid in the body of water with the submersible vehicle, introducing the submersible vehicle into the body of water prior to a release of the released fluid into the body of water.

3. The method of claim 1, wherein detecting the presence of the released fluid in the body of water comprises sensing rheological properties of the released fluid with one or more sensors of the submersible vehicle.

4. The method of claim 3, wherein detecting the presence of the released fluid in the body of water comprises:

comparing rheological properties sensed with the one or more sensors to a database of rheological properties associated with known fluids; and identifying the released fluid as one of the known fluids whose rheological properties correspond to the sensed rheological properties.

5. The method of claim 1, wherein detecting the presence of the released fluid in the body of water with the submersible vehicle comprises detecting the presence of the released fluid in the body of water with a plurality of submersible vehicles operating in concert with each other, each of the plurality of submersible vehicles coupled to the external storage tank by the conduit.

6. The method of claim 1, further comprising sensing for the presence of the released fluid while collecting the released fluid in the body of water.

7. A system for detecting a presence of a released fluid in a body of water and collecting the released fluid from the body of water, the released fluid released from a petroleum operation, the system comprising:

(A) an external storage tank;
(B) a submersible vehicle comprising:
 a plurality of sensors to detect a presence of the released fluid;
 an internal storage tank; and
 a fluid collection system configured to collect the released fluid from the body of water near the petroleum operation and transfer the released fluid from the internal storage tank to the external storage tank;
(C) a conduit coupled between the internal storage tank of the submersible vehicle and the external storage tank to conduct a flow of the released fluid; and
(D) one or more processors and a non-transitory computer-readable storage medium coupled to the one or more processors and storing programming instructions for execution by the one or more processors, the programming instructions instructing the one or more processors to:
 detect, by the plurality of sensors, the presence of the released fluid in the body of water near the petroleum operation;
 based on detecting the presence of the released fluid, operate the fluid collection system to collect the released fluid into the internal storage tank; and transfer the released fluid from the internal storage tank of the submersible vehicle to the external storage tank via the conduit.

8. The system of claim 7, wherein the plurality of sensors of the submersible vehicle comprise at least one of a temperature sensor, a conductivity sensor, a viscosity sensor, a density sensor, a resonator sensor, a microcapillary resonator, a thin-film bulk acoustic wave resonator, or a microelectro mechanical system to sense rheological properties of the released fluid near the petroleum operation.

9. The system of claim 8, wherein the programming instructions are further configured to instruct the one or more processors to:
compare the rheological properties sensed by the plurality of sensors to a database of rheological properties associated with known fluids; and
identify the released fluid as one of the known fluids whose rheological properties correspond to the sensed rheological properties.

10. The system of claim 9, wherein the known fluids are at least one of hydrocarbon, a drilling fluid, or a production chemical.

11. The system of claim 7, wherein the programming instructions are operable to instruct the one or more processors to direct the submersible vehicle to search for the presence of the released fluid in the body of water with another submersible vehicle, the submersible vehicles operating in concert with each other.

12. The system of claim 7, wherein the plurality of sensors are configured to sense for the presence of the released fluid while the fluid collection system is collecting the released fluid from the body of water.

13. The system of claim 7, further comprising a surface vessel, wherein the external storage tank is contained in, on, or within the surface vessel.

14. The system of claim 13, wherein the surface vessel is at least one of a ship, a barge, a buoyant tank, or an oil platform.

15. The system of claim 14, wherein the umbilical cord transfers electrical power from the surface vessel to the submersible vehicle and a sensor data, a propulsion data, a control information, an image data, or a status from the submersible vehicle to the surface vessel.

16. The system of claim 13, further comprising an umbilical cord tethering the submersible vehicle to the surface vessel.

17. The system of claim 13, wherein the one or more processors and the non-transitory computer-readable storage medium are positioned on the surface vessel.

18. The system of claim 7, wherein the one or more processors and the non-transitory computer-readable storage medium are positioned in the submersible vehicle.

19. The system of claim 7, wherein the fluid collection system comprises:
a piping system having an inlet open to the body of water and an outlet coupled to the conduit;
a first valve positioned in the piping system to control a flow of the released fluid from the body of water into the piping system;
a second valve positioned in the piping system to control a flow of the released fluid from the fluid collection system into the conduit;
a third valve positioned in the piping system to control a flow of the released fluid to and from the internal storage tank; and
a fluid pump fluidly coupled to the piping system to generate the flow of the released fluid from the body of water into the piping system, a flow of the released fluid from the fluid collection system into the conduit, and the flow of the released fluid to and from the internal storage tank based on a closed configuration or an open configuration of one or more of the first valve, the second valve, or the third valve.

20. The system of claim 19, further comprising:
a vent coupled to the internal storage tank, the vent fluidly coupling the internal storage tank to the body of water; and
a fourth valve positioned in the vent to control a flow of an initial fluid in the internal storage tank from the internal storage tank to the body of water.

21. The system of claim 20, further comprising a vent sensor coupled to the vent, the vent sensor configured to:
detect the released fluid in the vent; and
send a signal indicating a presence of the released fluid in the vent to the one or more processors and the non-transitory computer-readable storage medium to operate the fluid collection system based on the presence of the released fluid in the vent.

22. The system of claim 19, wherein the one or more processors and the non-transitory computer-readable storage medium to operate the fluid collection system are configured to operate the first valve, the second valve, the third valve, and the fluid pump to flow the released fluid directly from the body of water through the piping system to the conduit and on to a surface vessel which contains the external storage tank.

* * * * *